| United States Patent [19] | [11] Patent Number: 4,912,043 |
|---|---|
| Terasawa et al. | [45] Date of Patent: Mar. 27, 1990 |

[54] METHOD OF PREPARING L-MALIC ACID

[75] Inventors: Masato Terasawa; Terukazu Nara; Hideaki Yukawa; Hisashi Yamagata; Yukie Satoo, all of Ibaraki, Japan

[73] Assignee: Mitsubishi Petrochemical Co., Ltd., Tokyo, Japan

[21] Appl. No.: 864,212

[22] Filed: May 19, 1986

[30] Foreign Application Priority Data

May 17, 1985 [JP] Japan ................................ 60-105649
Aug. 28, 1985 [JP] Japan ................................ 60-187518

[51] Int. Cl.$^4$ ........................ C12P 7/46; C12N 15/00; C12N 1/00
[52] U.S. Cl. ................................ 435/145; 435/252.1; 435/172.1; 435/840
[58] Field of Search ............ 435/145, 840, 253, 172.1, 435/179, 180, 252.1

[56] References Cited

U.S. PATENT DOCUMENTS 3,922,195  11/1975  Chibata et al. ...................... 435/145

FOREIGN PATENT DOCUMENTS 57-26755   7/1982  Japan ................................ 435/145
59-28398  12/1984  Japan ................................ 435/145

OTHER PUBLICATIONS

Bergey's Manual of Determinative Bacteriology, Buchanan et al., (ed.) 8th ed., 1974, Williams and Wilkins, pp. 626-627.

Primary Examiner—Charles F. Warren
Assistant Examiner—Irene Marx
Attorney, Agent, or Firm—Oblon, Spivak, McClelland, Maier & Neustadt

[57] ABSTRACT

An aqueous solution containing fumaric acid is reacted in the presence of an aerobically cultured product of a microorganism belonging to the Brevibacterium genus and having resistance to α-aminobutyric acid, whereby L-malic acid is produced.

2 Claims, No Drawings

METHOD OF PREPARING L-MALIC ACID

FIELD OF THE INVENTION

This invention relates to a method of preparing L-malic acid in a higher yield. This invention also relates to a method of preparing L-malic acid using a microorganism very efficiently by inhibiting its enzymatic activity for a side-reaction which forms succinic acid but maintaining its fumarase activity. This acid is used for preparing medicines, etc., and it is expected that it will also be used in the preparation of food in the future.

BACKGROUND OF THE INVENTION

There are known methods which rely on fermentation for preparing L-malic acid. A microorganism having fumarase activity is cultivated in a culture medium containing fumaric acid and L-malic acid is collected from the product of cultivation. See, for example, Japanese Patent Publication No. 16547/66. These methods, however, require a large apparatus for fermentation and yet have a very low yield of L-malic acid. The acid prepared by these methods is, therefore, expensive.

There are also known methods which employ an enzyme. The fumarase in a microorganism having fumarase activity is used to prepare L-malic acid from fumaric acid or a salt thereof. See, for example, *The Journal of General and Applied Microbiology*, 6, 108–116 (1960), *European Journal of Applied Microbiology*, 3, 169–183 (1976) and Japanese Patent Publication Nos. 4511/62 and 1191/69. The preparation of L-malic acid on an industrial scale by these methods requires the use of a microorganism having a very high fumarase activity. It is, however, very difficult to separate any such microorganism from the natural world. This has been a great obstacle to the application of these methods on an industrial basis.

Both of these known methods also have a common problem which is due to the use of a microorganism. Succinic acid is often produced from fumaric acid as a by-product and is difficult to separate from L-malic acid efficiently. It is, therefore, important to prevent the formation of succinic acid as a by-product in order to prepare L-malic acid effectively on an industrial basis.

There are known a couple of methods for preventing the formation of succinic acid. According to one of them, a microorganism is immobilized and brought into contact with an organic solvent (Japanese Patent Publication No. 8396/77). According to the other method, an immobilized microorganism is brought into contact with bile acid (Japanese Patent Publication No. 31952/77). The use of an organic solvent, however, calls for special care from a safety standpoint and, therefore, special equipment. Bile acid is expensive. Moreover, it requires a long time for completing the necessary reaction. Therefore, both of these methods have been unsatisfactory from the standpoint of industrial application and there has been a strong demand for a simpler and less expensive method.

SUMMARY OF THE INVENTION

It is, therefore, an object of this invention to provide a method which can prepare L-malic acid from fumaric acid or a salt thereof very efficiently by preventing the formation of succinic acid as a by-product This object is attained by a method of preparing L-malic acid by reacting fumaric acid or a salt thereof with an enzyme in an aqueous solvent, wherein the enzyme is supplied by an aerobically cultured product of a microorganism belonging to the Brevibacterium genus and having α-aminobutyric acid resistance, or an appropriately treated product thereof.

The resistance of the microorganism to α-aminobutyric acid is preferably obtained or increased artificially. The cultured product of the microorganism or the treated product thereof is preferably heated in an aqueous solution of L-malic acid or a salt thereof so that no succinic acid may be produced, while the fumarase which the microorganism contains retains its activity. The use of such a microorganism makes it possible to produce L-malic acid from fumaric acid very efficiently. Therefore, this invention contributes greatly to the industrial production of L-malic acid.

DETAILED DESCRIPTION OF THE INVENTION

The method of this invention is characterized by employing a microorganism belonging to the Brevibacterium genus and having α-aminobutyric acid resistance. It may be a microorganism having such resistance obtained by accidental variation in the natural world, for example, *Brevibacterium flavum* MJ-233 which has been deposited with the Fermentation Research Institute, Agency of Industrial Science and Technology, Japan, under FERM BD1497 deposited on May 1, 1987 as disclosed in Japanese Patent Publication No. 26755/82. It is, however, preferable to employ a microorganism having such resistance obtained and/or increased artificially, for example, *Brevibacterium flavum* MJ-233-AB-41 which has been deposited with the Fermentation Research Institute Agency of Industrial Science and Technology, Japan, under FERM BP 1498 deposited on May 1, 1981 as disclosed in Japanese Patent Publication No. 28398/84

Although the microorganism can be used in a free form of bacterial cell, it is advantageous to immobilize bacterial cell or the enzyme (fumarase) which bacterial cell contains. It can be immobilized in a customary way. For example, it can be immobilized to a polyacrylamide or carrageenan gel or a high polymer film. It may be immobilized before or after it is subjected to the heat treatment which prevents the formation of succinic acid, as will hereinafter be described in further detail.

A microorganism having an artificially obtained or increased resistance to α-aminobutyric acid can be derived from one belonging to the Brevibacterum genus by a known method as will hereunder be described. A variation is produced from, for example, *Brevibacterium flavum* MJ-233 by applying ultraviolet rays to it or treating it with a chemical agent, such as N-methyl-N'-nitro-N-nitrosoguanidine. The resulting suspension is cultured in a culture medium plate containing 10 mg of α-amino-n-butyric acid per milliliter at a temperature of 30° C. for several days. The medium may contain 0.2 wt % of urea, 0.7 wt % of ammonium sulfate, 0.05 wt % of $KH_2PO_4$, 0.05 wt % of $K_2HPO_4$, 0.05 wt % of $MgSO_4.7H_2O$, 2 mg of NaCl per liter, 2 mg of $CaCl_2.2H_2O$ per liter, 2 mg of $FeSO_4.7H_2O$ per liter, 2 mg of $MnSO_4.4$–$6H_2O$ per liter and 2 mg of $ZnSO_4.7H_2O$ per liter, 200 μg of biotin per liter, 100 μg of thiamine hydrochloride per liter, 1.0 wt % of α-amino-n-butyric acid, 2.0 wt % of agar and 3 vol % of ethanol which is added after sterilization, whereby a large colony is produced. Tee colony is divided to provide a variation having resistance to α-aminobutyric acid or an increased resistance thereto.

In the content of this invention, the α-aminobutyric acid resistance of a microorganism is defined by a relative growth rate which is achieved when it is cultured under shaking at 30° C. for three days in a culture medium of the composition shown at Note 1 below, and further containing 2 wt % of α-aminobutyric acid. A microorganism having an artificially obtained and/or increased resistance to α-aminobutyric acid shows a relative growth rate of at least 15, or preferably at least 30. The relative growth rate can be expressed by the following equation:

$$\text{Relative growth rate} = \frac{\text{Growth rate O.D.}_{610} \text{ in a medium containing 2 wt \% of } \alpha\text{-AB}}{\text{Growth rate O.D.}_{610} \text{ in a medium containing no } \alpha\text{-AB}} \times 100$$

where α-AB stands for DL-α-aminobutyric acid.

Note 1: Composition of the culture medium and a method of culture:

The medium contained 0.2 wt % of urea, 0.7 wt % of ammonium sulfate, 0.05 wt % of $KH_2PO_4$, 0.05 wt % of $K_2HPO_4$, 0.05 wt % of $MgSO_4.7H_2O$, 0.05 wt % of yeast extract, 0.01 wt % of Casamino acid, 2 mg of $FeSO_4.7H_2O$ per liter, 2 mg of $MnSO_4.4-6H_2O$ per liter, 2 mg of NaCl per liter, 2 mg of $CaCl_2.2H_2O$ per liter, 2 mg of $ZnSO_4.7H_2O$ per liter, 22 μg of biotin per liter and 100 μg of thiamine hydrochloride per liter. Each amount of DL-α-aminobutyric acid shown in Table 1 below was added to the medium. 10 ml of the medium were placed in a large test tube having a diameter of 24 mm. The medium was sterilized at 120° C. for 10 minutes. A microorganism, such as *Brevibacterium flavum* MJ-233-AB-41, was seeded into the medium. After 0.3 ml (3 vol %) of ethanol had been added under sterilized conditions, the microorganism was cultured under shaking at 30° C. for three days.

Note 2: Growth rate O.D.$_{610}$ and relative growth rate:

The growth rate O.D.$_{610}$ was defined by the absorbance measured at a wavelength of 610 mμ by the method described in *Experimental Agricultural Chemistry* edited by the University of Tokyo, Faculty of Agriculture, Department of Agricultural Chemistry, Vol. 1, page 212, Asakura Shoten (1975). The relative growth rate was based on a standard value of 100 representing the growth rate O.D.$_{610}$ which was observed when no DL-α-aminobutyric acid had been added to the medium. The growth rates of *Brevibacterium flavum* MJ-233 and *Brevibacterium flavum* MJ-233-AB-41 which were obtained relative to DL-α-aminobutyric acid are shown in Table 1.

TABLE 1

| Amount of DL-α-Amino-butyric Acid Added (wt %) | Relative Growth Rate | |
|---|---|---|
| | MJ-233 | MJ-233-AB-41 |
| 0 | 100 | 100 |
| 1.0 | 50 | 60 |
| 1.5 | 30 | 50 |
| 2.0 | Below 5 | 40 |

According to this invention, the microorganism is cultured aerobically. There is no particular limitation to the composition of the culture medium which can be used. The medium may, for example, contain ethanol, methanol, n-paraffin or molasses as a source of carbon, ammonia, ammonium sulfate, ammonium chloride, ammonium nitrate or urea as a source of nitrogen, and potassium hydrogenphosphate, potassium dihydrogenphosphate or magnesium sulfate as an inorganic salt. The carbon and nitrogen sources and the inorganic salt may be used alone, or together after they have been mixed.

The medium may further contain a nutrient or nutrients, such as peptone, meat or yeast extract, corn steep liquor, Casamino acid and vitamins, if they are required for the growth of a microorganism.

The culture is carried out under the aerobic conditions which can, for example, be obtained by aeration or shaking. It is carried out at a temperature of 20° C. to 40° C. A preferred temperature range is from 25° C. to 35° C. The medium is required to maintain a pH of 5 to 10 throughout the culture. A preferred pH is in the vicinity of 7 or 8. An acid or alkali is added to the medium to adjust its pH.

The medium contains 1 to 5 vol % of a source of carbon, such as ethanol, when the culture is started. A preferred amount thereof is from 2 to 3 vol %. The culture s continued for a period of two to eight days. A preferred period is four or five days.

The cultured product contain fumarase having a high degree of enzymic activity. It makes it possible to produce L-malic acid from fumaric acid or a salt thereof, such as a sodium or calcium salt thereof, very efficiently.

The cultured product or any treated product thereof can be used for the production of L-malic acid by the reaction of the enzyme. In other words, it is possible to use cultured broth per se and any product obtained therefrom, such as a bacterial cell, a disrupted or ground product of the bacterial cell, and any immobilized product thereof, and autolyzed fluid of the bacterial cell.

The aerobically cultured product of a microorganism belonging to the Brevibacterium genus and having resistance to α-aminobutyric acid, or an appropriately treated product thereof is preferably used for the production of L-malic acid after it has been subjected to the treatment which prevents the formation of succinic acid. This treatment may be achieved by heating the cultured or treated product in a 0.01 to 5 M aqueous solution of L-malic acid having a pH of 4 to 10 at a temperature of 40° C. to 60° C. The solution preferably has an L-malic acid concentration of 0.01 to 0.3 M and a pH of 5 to 9. A preferred heating temperature is up to 55° C. The treatment is continued for a period of 10 minutes to 5 hours, depending on the concentration of the bacterial cell. The use of a temperature which is higher than 60° C. should be avoided, as it causes fumarase to lose its activity. The use of a lower temperature should also be avoided, as it fails to inhibit satisfactorily the side reaction which forms succinic acid. An L-malic acid concentration which is higher than 5 M is uneconomical. A concentration which is lower than 0.01 M fails to inhibit the side reaction satisfactorily.

The bacterial cell obtained as hereinabove described or an immobilized product thereof has a drastically low degree of activity which contributes to the formation of succinic acid. Therefore, it inhibits the formation of succinic acid and enables the efficient production of L-malic acid from fumaric acid or a salt thereof.

According to the method of this invention, fumaric acid or a salt thereof is reacted with the enzyme in the aerobically cultured product of the microorganism or any reacted product thereof in an aqueous solvent, preferably after it has been treated for inhibiting the formation of succinic acid. The reactant has a pH of 4 to 10. The reaction is usually carried out at a temperature of about 15° C. to about 60° C. for a period of about 0.5 to about 48 hours. A preferred reaction temperature is from about 20° C. to about 55° C.

The aqueous solvent may be water, or a 10 to 500 mM aqueous solution of a solvent, such as phosphoric or trishydrochloric acid buffer solution. An alkali, such as sodium, potassium or ammonium hydroxide, or an inorganic acid, such as hydrochloric or sulfuric acid, may be added to the reactant so that it may have a pH of 4 to 10.

Although there is no particular limitation to the amount of the fumaric acid or salt thereof which is subjected to the reaction, it is usually appropriate to employ 0.5 to 30% (wt/vol). Although there is no particular limitation to the amount of the cultured or treated product, either, it is usually possible to employ 0.5 to 10% (wt/vol).

A known method, such as adsorption and desorption using, for example, an ion exchange resin or active carbon, can be employed for separating L-malic acid from the reaction product and refining it.

The invention will now be described more specifically with reference to a number of examples thereof.

EXAMPLES 1 AND 2

A culture medium was prepared from 4.0 g of urea, 14.0 g of ammonium sulfate, 0.5 g of $KH_2PO_4$, 0.5 g of $K_2HPO_4$, 0.5 g of $MgSO_4.7H_2O$, 6 mg of $FeSO_4. 7H_2O$, 6 mg of $MnSO_4.4–6H_2O$, 1.0 g of yeast extract, 1.0 g of Casamino acid, 200 μg of biotin, 100 μg of thiamine hydrochloride and 1 liter of tap water. 10 ml of the medium were placed in each of a plurality of large test tubes having a diameter of 24 mm. The medium was sterilized at 120° C. for 10 minutes under pressure and 0.3 ml of ethanol was added thereto under sterilized conditions to prepare a preculture medium. A loopful of each of Brevibacterium flavum MJ-233 (Example 2) and Brevibacterium flavum MJ-233-AB-41 (Example 1) was innoculated in the preculture medium and cultured under shaking at 30° C. for 2 days.

100 ml of a medium which was equal in composition to the preculture medium were placed in each of two 500 ml Erlenmeyer flasks. After the medium had been sterilized at 120° C. for 10 minutes under pressure, 3 ml of ethanol were added to each flask under sterilized conditions to prepare a main culture medium. 1 ml of the precultured product of each of the two microorganisms was inoculated in the main culture medium and cultured under shaking at 30° C. for 3 days.

Water was added to each cultured product to adjust its $O.D._{610}$ value to 10.0 and a certain amount of bacterial cells was collected from 100 ml of each cultured product by 15 minutes of centrifugal separation at a speed of 4,000 rpm.

An aqueous solution of fumaric acid was prepared by adding 10 g of fumaric acid to 70 ml of water. After a 5 N solution of NaOH had been added to the solution to adjust its pH to 6.0, water was added thereto until it had a total volume of 100 ml. Then, 50 ml of the solution was placed in each of two 100 ml Erlenmeyer flasks. The bacterial cells were added to the solution in each flask and reacted therewith at 45° C. for 2 hours under shaking. Then, the bacterial cells were removed from the reaction product by 15 minutes of centrifugal separation at 4,000 rpm and the amount of L-malic acid in the supernatant was measured by means of a high pressure liquid chromatograph. It was 40 mg/ml when the bacterial cells were of Brevibacterium flavum MJ-233 (Example 2), and 82 mg/ml when the bacterial cells were of Brevibacterium flavum MJ-233-AB-41 having an artificially produced resistance to α-amino-n-butyric acid (Example 1).

A 6 N solution of HCl was added to 50 ml of each reaction product to adjust its pH to about 2 and it was passed through a column filled with a strongly basic resin of the $R_2CO_3$ type known as Amberlite IRA-400 (trade name of Rohm & Haas Co.), whereby L-malic acid was adsorbed by the resin. Then, a 1 N solution of ammonium carbonate was supplied to elute the acid and the eluate was concentrated to cause precipitation of coarse L-malic acid crystals. The crystals were washed in acetone and dried. The amount of the crystals which had been obtained from 50 ml of each reaction product was measured. It was 2.6 g in Example 1 and 1.2 g in Example 2.

REFERENCE EXAMPLE 1

A medium was prepared from 4.0 g of urea, 14.0 g of ammonium sulfate, 0.5 g of $KH_2PO_4$, 0.5 g of $K_2HPO_4$, 0.5 g of $MgSO_4.7H_2O$, 6 mg of $FeSO_4. 7H_2O$, 6 mg of $MnSO_4.4–6H_2O$, 1.0 g of yeast extract, 1.0 g of Casamino acid, 200 μg of biotin, 100 μg of thiamine hydrochloride and 1 liter of distilled water. 100 ml of the medium were placed in each of a plurality of 500 ml Erlenmeyer flasks. The medium was sterilized at 120° C. for 15 minutes under pressure and 2vol % of ethanol was added thereto. A loopful of Brevibacterium flavum MJ-33-AB-41was inoculated in the medium and cultured at 30° C. for 24 hours under shaking.

20 ml of the cultured broth were inoculated in liter of a medium in a 2-liter jar fermenter. This medium contained 23.0 g of ammonium sulfate, 0.5 g of $KH_2PO_4$, 0.5 g of $K_2HPO_4$, 50. g of $MgSO_4. 7H_2O$, 20 mg of $FeSO_4. 7H_2O$, 20 mg of $MnSO_4. 4–6H_2O$, 3 g of yeast extract, 3 g of Casamino acid, 200 μg of biotin and 100 μg of thiamine hydrochloride in 1,000 ml of distilled water The solution was cultured at 33° C. under aeration at a rate of 1 vvm, while a pH of 7.6 was maintained. The culture was continued for 30 hours, while ethanol was added from time to time in such a way as to maintain a concentration of 1 to 1.5 vol %.

The bacterial cells thereby produced were collected from the cultured broth by 15 minutes of centrifugal separation at a speed of 6,000 rpm. Then, 2.5 g of the bacterial cells were suspended in 50 ml of a 0.2 M aqueous solution of L-malic acid having a pH of 6.0 which had been prepared for inhibiting the side reaction which would form succinic acid. The suspension was divided into five equal amounts. They were heated at five different temperatures, respectively, ranging from 35° C. to 55° C. and having a difference of 5° C. from one another. Then, the bacterial cells were collected centrifugally and after they had been washed twice in a 0.1 M potassium phosphate buffer solution having a pH of 7.8, they were examined for fumarase activity and activity for succinic acid formation.

For the purpose of examination as to fumarase activity, the bacterial cells were suspended in 100 ml of a 1.0 M aqueous solution of fumaric acid having a pH adjusted to 7.0 by NaOH and were reacted at 45° C. for 2 hours and the L-malic acid thereby formed was reacted with 2,7-naphthalenediol in the presence of sulfuric acid. The amount of the L-malic acid was determined by the color which it had developed. The amount of the succinic acid which had been formed was determined by high pressure liquid chromatography.

The results are shown in Table 2 below. In Table 2, the value showing the activity of the enzyme at each temperature is based on a standard value of 100 representing the activity in the bacterial cells which were not treated with any L-malic acid solution for inhibiting the formation of succinic acid.

TABLE 2

| Temperature | Relative Activity | |
|---|---|---|
| (°C.) | L-Malic Acid | Succinic Acid |
| 35 | 135 | 40 |
| 40 | 161 | 23 |
| 45 | 207 | Below 2 |
| 50 | 176 | Below 2 |
| 55 | 71 | Below 2 |
| Untreated | 100 | 100 |

REFERENCE EXAMPLE 2

The culture procedure of Reference Example 1 was repeated for preparing bacterial cells. Five suspensions of bacterial cells were prepared by suspending 2.5 g of the bacterial cells in 50 ml of each of 0.1, 0.2, 0.4, 0.6 and 1 M aqueous solutions of L-malic acid each having a pH of 6.0. Each suspension was heated at 45° C. for 2 hours and the bacterial cells were collected centrifugally. The bacterial cells were washed twice in a 0.1 M potassium phosphate buffer solution having a pH of 7.8 and examined for fumarase activity and activity for succinic acid formation. The results are shown in Table 3 below.

TABLE 3

| Concentration of L-Malic Acid | Relative Activity | |
|---|---|---|
| (M) | L-Malic Acid | Succinic Acid |
| 0.1 | 185 | Below 0.01 |
| 0.2 | 204 | 0.01 |
| 0.4 | 126 | 60 |
| 0.6 | 97 | 84 |
| 1.0 | 105 | — |
| Untreated | 100 | 100 |

EXAMPLE 3

The culture procedure of Reference Example 1 was repeated for preparing bacterial cells and a suspension thereof. They were reacted at 45° C. for 2 hours under shaking so that the formation of succinic acid might be inhibited. Then, the bacterial cells were collected by centrifugal separation and washed twice in a 1.0 M aqueous solution of fumaric acid having its pH adjusted to 7.0 by NaOH. The bacteria cells were, then, added to 100 ml of the same fumaric acid solution in a 200 ml Erlenmeyer flask and reacted at 45° C. for 2 hours under shaking. Upon completion of the reaction, the bacterial cells were removed from the solution by centrifugal separation and the concentration of L-malic acid in the remaining solution was determined by colorimetry. For this purpose, the procedure of Reference Example 1 was repeated. The amount of the succinic acid which had been formed was determined by high pressure liquid chromatography.

The results are shown in Table 4 together with the results which were obtained when the bacterial cells had not been treated with any L-malic acid solution.

TABLE 4

| | Yield of L-Malic Acid (%) | Yield of Succinic Acid (%) |
|---|---|---|
| Treated bacterial cells | 78 | Below 0.2 |
| Untreated bacterial cells | 44 | 30 |

Yield: Mol % relative to fumaric acid.

While the invention has been described in detail and with reference to specific embodiments thereof, it will be apparent to one skilled in the art that various changes and modifications can be made therein without departing from the spirit and scope thereof.

What is claimed is:

1. A method of preparing L-malic acid, comprising:
   prior to reacting fumaric acid with *Brevibacterium flavum* MJ-233-AB-41 (FERM-BP-1498) having an artificially acquired and/or increased resistance to α-aminobutric acid, heat treating cultured bacterial cells of said microorganism in an aqueous solution containing L-malic acid or a salt thereof at a temperature of 40° C. to 60° C. for a time ranging from 10 minutes to 5 hours; and
   allowing fumaric acid to react in an aqueous solution containing said heat treated microorganism, thereby producing L-malic acid.

2. The method of claim 1, wherein said solution in which said product is heat treated has a pH of 4 to 10 and an L-malic acid concentration of 0.01 to 5 M.

* * * * *